(12) United States Patent
Troha et al.

(10) Patent No.: US 7,501,452 B2
(45) Date of Patent: Mar. 10, 2009

(54) TREATMENT OF XEROSTOMIA

(75) Inventors: Janice Mary Troha, Boulder, CO (US); Victoria Jean Abbas, Westminster, CO (US); Gary Joseph Rosenthal, Lafayette, CO (US); Wren Henderson Schauer, Boulder, CO (US)

(73) Assignee: Endo Pharmaceuticals Inc., Chadds Ford, PA (US)

( * ) Notice: Subject to any disclaimer, the term of this patent is extended or adjusted under 35 U.S.C. 154(b) by 0 days.

(21) Appl. No.: 11/605,983

(22) Filed: Nov. 29, 2006

(65) Prior Publication Data

US 2007/0128284 A1 Jun. 7, 2007

Related U.S. Application Data

(60) Provisional application No. 60/740,711, filed on Nov. 30, 2005.

(51) Int. Cl.
*A61K 31/195* (2006.01)
(52) U.S. Cl. .................................................... 514/562
(58) Field of Classification Search ................. 514/562
See application file for complete search history.

(56) References Cited

U.S. PATENT DOCUMENTS

| | | | |
|---|---|---|---|
| 3,091,569 A | 5/1963 | Sheffner |
| 4,176,197 A | 11/1979 | Olson |
| 4,188,373 A | 2/1980 | Krezanoski |
| 4,512,968 A | 4/1985 | Komiyama et al. |
| 4,615,697 A | 10/1986 | Robinson |
| 4,708,965 A | 11/1987 | Morgan |
| 4,724,239 A | 2/1988 | Morgan |
| 4,918,224 A | 4/1990 | Krimmer et al. |
| 4,946,870 A | 8/1990 | Partain et al. |
| 4,968,506 A | 11/1990 | Appelgren et al. |
| 5,061,729 A | 10/1991 | Kincses et al. |
| 5,071,644 A | 12/1991 | Viegas et al. |
| 5,143,731 A | 9/1992 | Viegas et al. |
| 5,221,722 A | 6/1993 | Sehm |
| 5,286,480 A | 2/1994 | Boggs et al. |
| 5,296,500 A | 3/1994 | Hillebrand |
| 5,300,494 A | 4/1994 | Brode, II et al. |
| 5,346,703 A | 9/1994 | Viegas et al. |
| 5,358,705 A | 10/1994 | Boggs et al. |
| 5,447,712 A | 9/1995 | White et al. |
| 5,458,879 A | 10/1995 | Singh et al. |
| 5,472,704 A | 12/1995 | Santus et al. |
| 5,490,978 A | 2/1996 | Spaltro et al. |
| 5,510,101 A | 4/1996 | Stroppolo et al. |
| 5,580,577 A | 12/1996 | Herzenberg et al. |
| 5,593,683 A | 1/1997 | Viegas et al. |
| 5,597,849 A | 1/1997 | McGinity et al. |
| 5,635,489 A | 6/1997 | Haley |
| 5,637,616 A | 6/1997 | Sharpe et al. |
| 5,707,635 A | 1/1998 | Deckner et al. |
| 5,744,155 A | 4/1998 | Friedman et al. |
| 5,807,894 A | 9/1998 | Stroppolo et al. |
| 5,817,625 A | 10/1998 | Haley |
| 5,843,881 A | 12/1998 | Dubois et al. |
| 5,861,174 A | 1/1999 | Stratton et al. |
| 5,869,029 A | 2/1999 | Graff-Andersen et al. |
| 5,904,927 A | 5/1999 | Amiji |
| 5,939,485 A | 8/1999 | Bromberg et al. |
| 5,958,443 A | 9/1999 | Viegas et al. |
| 5,993,846 A | 11/1999 | Friedman et al. |
| 6,013,632 A | 1/2000 | Jones et al. |
| 6,025,326 A | 2/2000 | Steinberg et al. |
| 6,107,281 A | 8/2000 | Jones et al. |
| 6,117,415 A | 9/2000 | Schwarz |
| 6,126,930 A | 10/2000 | Dubois et al. |
| 6,150,472 A | 11/2000 | Engbers |
| 6,159,485 A | 12/2000 | Yu et al. |
| 6,159,491 A | 12/2000 | Durrani |
| 6,194,382 B1 | 2/2001 | Crain et al. |
| 6,197,331 B1 | 3/2001 | Lerner et al. |
| 6,207,703 B1 | 3/2001 | Ponikau |
| 6,228,347 B1 | 5/2001 | Hersh |
| 6,231,889 B1 | 5/2001 | Richardson et al. |
| 6,255,502 B1 | 7/2001 | Penkler et al. |
| 6,258,342 B1 | 7/2001 | Harcum et al. |
| 6,291,500 B2 | 9/2001 | Ponikau |
| 6,297,337 B1 | 10/2001 | Marchant et al. |
| 6,309,663 B1 | 10/2001 | Patel et al. |

(Continued)

FOREIGN PATENT DOCUMENTS

WO  WO 94/03157  2/1994

(Continued)

OTHER PUBLICATIONS

De Flora et al. (2001) Mechanisms of N-acetylcysteine in the prevention of DNA damage and cancer, with special reference to smoking-related end-points. Carcinogenesis. vol. 22 No. 7, 999-1013.

(Continued)

*Primary Examiner*—Raymond J Henley, III
(74) *Attorney, Agent, or Firm*—Pamela D. Politis (57) ABSTRACT

Xerostomia is treated with a sulfur-containing antioxidant, such as N-acetylcysteine. Delivery compositions including polyoxyalkylene block copolymers may be used, which may be formulated to exhibit reverse-thermal viscosity behavior.

23 Claims, 2 Drawing Sheets

U.S. PATENT DOCUMENTS

| | | |
|---|---|---|
| 6,316,011 B1 | 11/2001 | Ron et al. |
| 6,319,513 B1 | 11/2001 | Dobrozsi |
| 6,323,189 B1 | 11/2001 | Hardinge-Lyme |
| 6,346,272 B1 | 2/2002 | Viegas et al. |
| 6,350,785 B2 | 2/2002 | Gehlsen |
| 6,432,415 B1 | 8/2002 | Osborne et al. |
| 6,458,373 B1 | 10/2002 | Lambert et al. |
| 6,468,548 B1 | 10/2002 | Kis |
| 6,479,068 B1 | 11/2002 | Sherratt et al. |
| 6,503,955 B1 | 1/2003 | Dobrozsi et al. |
| 6,509,028 B2 | 1/2003 | Williams et al. |
| 6,511,800 B1 | 1/2003 | Singh |
| 6,562,802 B2 | 5/2003 | Johannson et al. |
| 6,565,895 B2 | 5/2003 | Goddard et al. |
| 6,620,428 B1 | 9/2003 | Hoeck et al. |
| 6,623,754 B2 | 9/2003 | Guo et al. |
| 6,685,917 B2 | 2/2004 | Rosenthal et al. |
| 6,743,422 B1 | 6/2004 | Nahri et al. |
| 6,790,827 B2 | 9/2004 | Grissom et al. |
| 6,797,729 B1 | 9/2004 | Byrne et al. |
| 6,841,578 B2 | 1/2005 | Sonis |
| 7,033,606 B1 | 4/2006 | Besse et al. |
| 2001/0018059 A1 | 8/2001 | Gehlsen |
| 2001/0025027 A1 | 9/2001 | Sonis |
| 2002/0013331 A1 | 1/2002 | Williams et al. |
| 2002/0095001 A1 | 7/2002 | Gehlsen |
| 2002/0168334 A1 | 11/2002 | Jacob et al. |
| 2003/0064913 A1 | 4/2003 | Sonis |
| 2003/0229141 A1 | 12/2003 | Yu et al. |
| 2004/0062764 A1 | 4/2004 | Neuwelt et al. |
| 2004/0198841 A1* | 10/2004 | Neuwelt .................... 514/711 |
| 2006/0177523 A1 | 8/2006 | Neuwelt et al. |

FOREIGN PATENT DOCUMENTS

| | | |
|---|---|---|
| WO | WO 96/00060 | 1/1996 |
| WO | WO 97/20576 | 6/1997 |
| WO | WO 98/06438 | 2/1998 |
| WO | WO 99/32135 | 7/1999 |
| WO | WO 99/63986 | 12/1999 |
| WO | WO 01/66108 A1 | 9/2001 |
| WO | WO 01/74324 A1 | 10/2001 |
| WO | WO 02/36098 A1 | 5/2002 |
| WO | WO 02/41837 A2 | 5/2002 |
| WO | WO 02/41837 A3 | 5/2002 |
| WO | WO 02/092103 A1 | 11/2002 |
| WO | WO 02/100395 A1 | 12/2002 |

OTHER PUBLICATIONS

Liu et al. (1998) Gluthathione Regulation of Neutral Sphingomyelinase in Tumor Necrosis Factor-α-induces Cell Death. J. Biological Chemistry. vol. 23, No. 18, 11313-11320.

Peristeris et al. (1992) N-acetylcysteine and Gluthathione as Inhibitors of Tumor Necrosis Factor Production. Cellular Immunology. vol. 140, 390-399.

Wadleigh, R. et al. (1992) Vitamin E in the Treatment of Chemotherapy-Induced Mucositis. The American Journal of Medicine. vol. 92, 481-484.

Blonder JM, et al. Topical Bioadhesive (BiAD) Antioxidants Reduce the Severity of Experimental Radiation-Induced Oral Mucositis. Poster. 2001 ASCO Annual Meeting.

ISR from PCT/US06/045781 Jan. 21, 2008.

Kayama, Mamoru: "Effects of a radioprotective agent (reduced glutathione) upon radiation stomatitis", Kanazawa Irigaku Sosho, XP002463743, 1969, vol. 83, pp. 23-36.

Crispian Scully et al., Oral Health Care for the Cancer Patient, Oral Oncol, Eur J Cancer, 1996, pp. 281-292, vol. 32B, No. 5.

Stephen T. Sonis, DMD, DMSc, A Biological Approach to Mucositis, J Support Oncol, Jan./Feb. 2004, pp. 21-36, vol. 2 No. 1.

Fred R. Burlage et al., Parotid and submandibular/sublingual salivary flow during high dose radiotherapy, Radiotherapy and Oncology 61, (2001), pp. 271-274.

James W. Denham et al., Do acute mucosal reactions lead to consequential late reactions in patients with head and neck cancer, Radiotherapy and Oncology 52, (1999) pp. 157-164.

A. Vissink et al., Oral Sequelae of Head and Neck Radiotherapy, Crit Rev Oral Biol Med 14(3), (2003), pp. 199-212.

A. Vissink et al., Prevention and Treatment of the Consequences of Head and Neck Radiotherapy, Crit Rev Oral Biol Med 14(3), (2003), pp. 213-225.

Cooper et al, Postoperative Concurrent Radiotherapy and Chemotherapy for High-Risk Squamous-Cell Carcinoma of the Head and Neck, N Engl J Med, (2004), pp. 1937-1944, vol. 350.

* cited by examiner

FIGURE 1

Figure 2: Percentage Incidence of Xerostomia

TREATMENT OF XEROSTOMIA

CROSS-REFEENCE TO RELATED APPLICATIONS

This application claims the benefit of prior U.S. Provisional Patent Application No. 60/740,711 entitled TEATMENT OF XEROSTOMIA, filed Nov. 30, 2005, each and every portion of the contents of which are incorporated herein by reference as if set forth herein.

FIELD OF THE INVENTION

This invention relates to treatment of xerostomia, including without limitation methods for treating for xerostomia and active agents and formulations, and use of such active agents and formulations, for treatment for xerostomia and for preparation of formulations for treatment for xerostomia.

BACKGROUND OF THE INVENTION

Xerostomia is defined as dry mouth and/or thickened saliva resulting from altered, reduced or absent saliva flow. Saliva is a viscous clear fluid secreted from the salivary glands, which include for example the parotid, submaxillary, sublingual and smaller mucous glands in the oral cavity. Saliva is made up of various enzymes, proteins, small organic molecules, electrolytes and constituents of nonsalivary origin in a water matrix. Saliva possesses many important functions including antimicrobial activity, mechanical cleansing properties, maintaining oral pH between 6 and 7.4, removal of food from the oral cavity, lubrication of the oral cavity, remineralization and maintenance of the oral mucosa integrity. Saliva also provides a first defense against chemical, microbial and infectious attack.

Common causes of xerostomia include medications, irradiation of the head and neck and organic and psychogenic diseases. Some classes of medications that may cause xerostomia include anorectics, anticholinergics, antidepressants, antihistamines, antihypertensives, antiparkinson medications, antipsychotics, antispasmodics, decongestants, diuretics, sedative/hypnotics and narcotic analgesics. Approximately 1800 drugs in 80 drug classes have been reported to possess the capacity to cause xerostomia. Of the 50 most frequently prescribed brand name drugs in the U.S. in 2003, 64% were reported to be xerogenic. Xerostomia can effect patients in all age groups however, it is important to point out that it is the elderly population (described as individuals who are older than 65 years of age) who are most affected, because of their proportionally higher use of these types of drugs, often on a daily basis.

Sjögren's syndrome (SS) is reported as the most common disease causing xerostomia. SS is a chronic inflammatory disease that largely affects post menopausal women. Other rheumatoid conditions that may cause SS include rheumatoid arthritis, systemic lupus erythematosus and scleroderma. Organic diseases that have been reported to cause xerostomia include diabetes mellitus, hypertension, cystic fibrosis and neurological diseases such as Bell's palsy, cerebral palsy and trauma. Also, any condition that leads to dehydration has potential to produce xerostomia.

Radiotherapy plays a significant role in the management of head and neck cancer. An estimated 39,000 new cases of head and neck cancer occur annually in the U.S. and the incidence of xerostomia in those patients can exceed 80%. Acute oral mucositis and acute and chronic xerostomia are the most common and clinically significant toxicities arising from head and neck irradiation. Xerostomia can be a lifelong sequelae of head and neck radiation. It has been hypothesized that the irradiation of the head and neck may cause changes to the salivary glands that may or may not be permanent. Xerostomia has a clinically adverse impact on the patient and disrupts eating and sleeping as well as causing nausea.

Initial symptoms of xerostomia include problems eating, speaking and swallowing and a constant need for fluids. Chewing of dry foods may also become difficult. Patients with xerostomia complain of taste disorders, sore throat, burning sensations, increase in caries, inflammation of the gum line, and fissures of the lips. With prolonged and severe xerostomia chances of tooth loss with a risk of osteonecrosis greatly increase. As the oral mucosa becomes dehydrated, patients using dental appliances have problems with appliance retention, develop sores and complain of the tongue sticking to the palate of the mouth. As the oral pH decreases and the normal mouth flora are altered, the oral mucosa becomes dry and sticky and several opportunistic microorganisms increase in concentration, such as *Candida albicans*.

The clinical diagnosis of xerostomia is usually made when the patient experiences dry mouth, thickened saliva, decreased salivary flow and a sudden onset of caries. The saliva may appear ropy and foamy on teeth and root surfaces.

Treatment of xerostomia has been directed toward the control of dental decay, relief of symptoms and increasing the saliva flow. The treatments available range from over the counter (OTC) medications to prescription drugs. Truly effective compounds appear to be few. As previously noted, a larger number of prescription drugs cause or exacerbate xerostomia. Fluoride gels and rinses are used to increase tooth resistance to caries by promoting remineralization of the teeth. Artificial saliva and saliva substitutes are used in the form of solutions, sprays and lozenges to replace moisture and lubricate the mouth, however, they must be used frequently and consistently as they do not stimulate salivary function. The prescription drugs available include pilocarpine, cevimeline, anethole trithione, yohimbine, human interferon alpha and amifostine. Pilocarpine (Salagen) is a cholingeric parasympathomimetic agent, which may stimulate salivary flow and produce clinical benefits in some patients as well as cause adverse effects with other drugs. Salagen dispensed in a tablet form stimulates salivary secretions but can also increase secretions from a number of other glands. Pilocarpine has been investigated for use as a treatment for oral mucositis but was found to be ineffective in the management of oral mucositis. Cevimeline a cholinergic agonist is another systemic agent that appears to help certain patient populations. Cevimeline, dispensed in a tablet form, stimulates salivary secretions but can result in excessive sweating and nausea. Anethole trithione is a cholagogue that stimulates salivary flow in drug-induced xerostomia. Some patients receiving the bile secretion-stimulating drug see improvements with salivary flow rates, trials in patients with SS show conflicting results. Yolimbine is an alpha-2 adrenergic antagonist that can increase saliva flow and maybe more effective than anethole trithione in SS populations. Human interferon alpha is currently in clinical trials for use as a primary treatment for SS. Amifostine (Ethyol) has been approved for use for the treatment of radiation-induced xerostomia, however, a study of this compound for the indication of oral mucositis found that amifostine did not reduce oral mucositis.

Even though there has been some success reported in treating xerostomia, as noted above, given the large number of patients suffering from xerostomia annually and the larger number of patients undergoing cancer therapy, who often receive multiple cycles of radiation therapy and/or chemotherapy, there is a significant need for improved treatments for xerostomia. The present invention is directed to this significant need.

SUMMARY OF THE INVENTION

The invention involves use of a sulfur-containing antioxidant for treatment of xerostomia.

One aspect of the invention concerns a method for treating for xerostomia. The method comprises administering to a human (or other mammalian) patient a therapeutically effective amount of an active agent for treating xerostomia, wherein the active agent is a sulfur-containing antioxidant effective for treating for xerostomia.

Another aspect of the invention concerns delivery compositions useful for administration of the sulfur-containing antioxidant.

Other aspects of the invention concern use of a sulfur-containing antioxidant for treatment for xerostomia and use of a sulfur-containing antioxidant for preparation of a medicament for treatment of xerostomia.

DETAILED DESCRIPTION OF THE INVENTION

As used herein, "treating", or "treatment", for xerostomia includes all pharmaceutical administrations designed to prevent, reduce the severity of, cure or alleviate symptoms of xerostomia, including without limitation prophylactic (preventive) treatment aimed at preventing occurrence of the condition, curative treatment aimed at curing an occurrence of the condition and palliative treatment aimed at relieving or lessening the severity of symptoms of the condition.

As used herein, "NAC" means N-acetylcysteine, which is the acetylated variant of the naturally-occurring amino acid L-cysteine. A precursor of reduced glutathione (GSH), NAC becomes converted to circulating cysteine by de-acetylation which is then available for GSH synthesis as needed.

As used herein, "biocompatible" means not having toxic or injurious effects on biological function in humans.

As used herein, "reverse-thermal gel transition temperature", or simply "transition temperature", refers to a temperature at which a material having reverse-thermal gelation properties changes physical form from a liquid to a gel as the temperature of the material is increased from below to above the temperature, and changes physical form from a gel to a liquid as the temperature is decreased from above to below the temperature.

As used herein, "reverse-thermal gelation property" refers to a property of a material, such as a reverse-thermal gelation polymer/liquid vehicle combination or the delivery composition, as the case may be, to change physical form from a liquid to a gel with increasing temperature. As used herein, a gel includes gelatinous and semi-solid materials that are generally not significantly flowable.

As used herein, the terms "reverse-thermal viscosity property" and "reverse-thermal viscosity behavior" each refers to a property of a component or components, and in particular a biocompatible polymer/liquid vehicle (typically water) combination, in a delivery composition to undergo a viscosity increase with increasing temperature across at least some temperature range. A reverse-thermal gelation property is one type of reverse-thermal viscosity behavior in which a component or components, and in particular a biocompatible polymer/liquid vehicle (typically water) combination, in a delivery composition, change from a liquid form to a gel form as the temperature is raised from below to above a reverse-thermal gel transition temperature.

As used herein, "reverse-thermal gelation polymer" refers to a polymer capable of interacting with a liquid vehicle, and particularly water, so that the polymer/liquid vehicle combination exhibits a reverse-thermal gelation property when the polymer and liquid vehicle are combined in at least some proportion. It will be appreciated that not all combinations of a reverse-thermal gelation polymer with the corresponding liquid vehicle in all proportions or in the presence of all other additives will exhibit reverse-thermal viscosity behavior (including a reverse-thermal gelation property) at all or within a targeted temperature range of interest, but for any appropriate reverse-thermal gelation/liquid vehicle pair, simple screening experiments can be performed to test formulation for reverse-thermal viscosity behavior by subjecting the formulation to increasing temperatures within the range of temperatures of interest.

The xerostomia therapeutic is a pharmaceutical substance that provides, alone or in combination with other components, a therapeutic effect for at least one of preventing, reducing the severity of, curing or alleviating symptoms of xerostomia. In that regard, the therapeutic effect may be due to the direct action of the pharmaceutical substance, or may be due to one or more other materials activated by the pharmaceutical substance or for which the pharmaceutical substance is a precursor.

The active agent, or xerostomia therapeutic, is a sulfur-containing antioxidant, preferably including sulfur in at least one constituent group selected from thiol, thioether, thioester, thiourea, thiocarbamate, disulfide and sulfonium, with thiol-containing antioxidants (also referred to as sulfhydryl-containing antioxidants) being particularly preferred. Some examples of preferred sulfur-containing antioxidants include N-acetylcysteine (NAC), glutathione, S-carboxymethylcysteine, methylmethionine sulfonium chloride, L-2-oxothiazolidine-4-carboxylic acid (Procysteine), lipoic acid and S-allyl cysteine. The sulfur-containing antioxidant, as formulated in a delivery composition for use, will be effective for use for treatment for xerostomia. It will be readily appreciated that not all sulfur-containing antioxidants, and not all formulations of a given sulfur-containing antioxidant, may be effective or effective in the same degree for treatment of xerostomia, but that the efficacy of any particular sulfur-containing antioxidant is readily determinable by those skilled in the art through experimentation and testing routinely performed on pharmaceutical products.

In one preferred embodiment, the sulfur-containing antioxidant is a precursor for biosynthesis of glutathione in the patient, such as by providing cysteine or a precursor for cysteine for glutathione biosynthesis. In this embodiment, the xerostomia therapeutic promotes the production of glutathione. Examples of sulfur-containing antioxidants that are precursors for glutathione biosynthesis include NAC, Procysteine, lipoic acid, S-allyl cysteine, and methylmethionine sulfonium chloride.

Particularly preferred for use as the xerostomia therapeutic is NAC.

Delivery of the xerostomia therapeutic may be accomplished via a variety of routes and administration techniques. Administration may be systemic or local using any convenient technique. Systemic administration may be accomplished for example, through ingestion of a capsule, pill or a liquid formulation. Local delivery may be accomplished for example by subcutaneous placement in the vicinity of at least one of the salivary glands (preferably by injection) or by direct delivery to at least one of the salivary glands, such as through injection of a delivery formulation directly into the gland. One preferred route for administration is via mucosal delivery accomplished through direct contact of a delivery formulation with the mucosa of interest, such as via nasal or oral mucosa. For mucosal delivery, the delivery formulation is preferably in the form of a liquid when administered, which may be in the form of a mouth rinse solution for oral mucosa or in the form of a mist of droplets for intranasal administration to contact nasal mucosa. A particularly preferred route of delivery is mucosal delivery through direct contact with mucosal surfaces within the oral cavity, referred to herein as oral mucosal delivery.

The xerostomia therapeutic is typically administered in a delivery formulation, or delivery composition, suitable for the selected administration technique. The delivery composition includes the xerostomia therapeutic and one or more other components formulated in a manner consistent with the selected administration technique/delivery route, provided that the other components are not incompatible with the intended performance of the xerostomia therapeutic. Nonlimiting examples of some other components that may be included in a delivery composition include one or more of the following: liquid vehicles, rheology modifiers (such as thickening agents or reverse-thermal gelation polymers), penetration enhancers, bioadhesive agents, stabilizers for the xerostomia therapeutic or another component (such as sucrose, salts and pH adjusting agents), preservatives (such as antioxidants such as butylated hydroxytoluene, antifungals, and antibacterials), and taste masking components. Inclusion of taste masking components is particularly desirable when administration is via oral mucosal delivery. Nonlimiting examples of taste masking components include fruit flavorings (and particularly citrus flavorings, such as a lemon flavor provided by addition of lemon juice or a lemon extract), mint flavorings, salt, or sugars. These examples are intended to provide some guidance as to some possible components for inclusion in a delivery formulation, and not to expressly or impliedly limit the type or number of other components that may be added.

The delivery composition can be in any convenient form, for the intended administration technique/delivery route. In a preferred embodiment, the delivery composition is in the form of a flowable fluid medium at the time of administration. For example, for oral mucosal delivery, the delivery composition is preferably sufficiently fluid in character that it can be accepted in the oral cavity and swished in the manner of an oral rinse. In this situation, the delivery composition will typically include as its largest constituent a carrier liquid, which imparts desired flowability to the delivery composition. The carrier liquid may be any convenient liquid, and may include only a single liquid component or may be a multi-component liquid mixture. Most often, the carrier liquid will be entirely or largely comprised of water, which is often added for example in the form of a saline buffer solution or some other convenient aqueous liquid solution. The carrier liquid may be organic in character, or may include both organic and aqueous components. The carrier liquid can be a solvent of dispersion medium containing, for example, one or more of water, ethanol, polyol (e.g., glycerol, propylene glycol, and liquid polyethylene glycol, and the like), and suitable mixtures thereof. In a preferred embodiment, the xerostomia therapeutic is dissolved in the carrier liquid at the time of administration to the patient.

A particularly preferred and advantageous delivery composition, which is versatile for a variety of administration techniques and delivery routes, and is particularly well suited for oral mucosal delivery, includes a biocompatible, polyoxyalkylene block copolymer. In a preferred implementation of this embodiment, the polyoxyalkylene block copolymer is a reverse-thermal gelation polymer selected for and incorporated into the delivery composition in a manner to impart reverse-thermal viscosity behavior (which may or may not include a reverse-thermal gelation property). As a further enhancement, the reverse-thermal viscosity behavior is such that the viscosity of the delivery composition increases with increasing temperature in the vicinity of human physiological temperature, which is typically about 37° C. In this way, the delivery composition can be administered as a lower viscosity flowable fluid medium at a cool temperature, and the viscosity of the delivery composition will increase as the delivery composition is warmed toward physiological temperature. In one embodiment, the delivery composition, and the xerostomia therapeutic, are at a temperature when administered to the patient that is in a range having a lower limit selected from the group consisting of 1° C. and 2° C. and an upper limit selected from the group consisting of 20° C., 15° C., 10° C. and 8° C. The delivery composition including a polyoxyalkylene block copolymer is sometimes referred to herein for convenience as a "POA formulation" and such a POA formulation that includes reverse-thermal viscosity behavior is sometimes referred to herein for convenience as a "reverse-thermal viscosity POA formulation."

As yet a further enhancement, a reverse-thermal viscosity POA formulation is formulated to exhibit reverse-thermal viscosity behavior within a temperature range having a lower limit selected from the group consisting of 1° C. and 2° C. and an upper limit selected from the group consisting of 37° C., 25° C., 20° C., 15° C., 10° C. and 8° C. For example, the reverse-thermal viscosity POA formulation may be refrigerated to the desired reduced temperature immediately prior to administration. By exhibiting reverse-thermal viscosity behavior within the temperature range, it is meant only that the viscosity of the reverse-thermal viscosity POA formulation increases with increasing temperatures over some temperatures within the range, and not that the reverse-thermal viscosity POA formulation must exhibit the reverse-thermal viscosity behavior over all temperatures of the range. When the reverse-thermal viscosity behavior includes a reverse-thermal gelation property, the reverse-thermal viscosity POA formulation preferably includes a reverse-thermal gel transition temperature within the noted temperature range.

It should be appreciated that, if desired, a reverse-thermal gelation polymer and liquid vehicle can be incorporated into the delivery composition in such proportions that the delivery composition does not have a reverse-thermal gelation property, or does not even exhibit reverse-thermal viscosity behavior. For most situations, however, it is preferred that delivery compositions including a reverse-thermal gelation polymer also exhibit reverse-thermal viscosity behavior.

With reverse-thermal viscosity behavior (which may or may not involve reverse-thermal gelation), the reverse-thermal viscosity POA formulation can be administered to a patient at a cool temperature, as noted above, which provides a beneficial 'cold' feeling upon tissue, such as in the oral cavity or esophagus, of the patient following administration. Also the reverse-thermal viscosity POA formulation tends to become more viscous, and possibly even gelatinous depending upon the concentration of polyoxyalkylene block copolymer used, as the reverse-thermal viscosity POA formulation warms toward physiological temperature, depending upon the rapidity with which the reverse-thermal viscosity POA formulation is diluted by biological fluids.

Preferred polyoxyalkylene block copolymers for use in delivery compositions for delivering the xerostomia therapeutic are polyoxyethylene-polyoxypropylene block copolymers. Examples of some polyoxyalkylene block copolymers include Pluronic™ F68 (a poloxamer 188), Pluronic™ F127 (a poloxamer 407), Pluronic™ L121 (a poloxamer 401), and Pluronic™ L101 (a poloxamer 331), and Tetronic™ T1501 (a poloxamine). Pluronic™ and Tetronic™ are trademarks of BASF Corporation. Furthermore, more than one of these and/or other polyoxyalkylene block copolymers may be included in the delivery composition. Also, other polymers and/or other additives may also be included in the delivery composition to the extent the inclusion is not inconsistent with the desired characteristics of the delivery composition. Furthermore, these polymers may be mixed with other polymers or other additives, such as sugars, to vary the transition temperature range, typically in aqueous solutions, at which reverse-thermal viscosity behavior occurs.

As will be appreciated, any number of polyoxyalkylene block copolymers may now or hereafter exist that are capable of being used in the delivery composition, and such polymers are specifically intended to be within the scope of the present invention when incorporated into the delivery composition.

A polyoxyalkylene block copolymer is a polymer including at least one block (i.e. polymer segment) of a first polyoxyalkylene and at least one block of a second polyoxyalkylene, although other blocks may be present as well. Polyoxyethylene-polyoxypropylene block copolymers (sometimes referred to herein for convenience as "POE-POP block copolymers") are one class of preferred polyoxyalkylene block copolymers in POA formulations. Also, for reverse-thermal viscosity POA formulations, the reverse-thermal gelation polymer is preferably a POE-POP block copolymer. POE-POP block copolymers include at least one block of a polyoxyethylene and at least one block of a polyoxypropylene, although other blocks may be present as well. A polyoxyethylene block may generally be represented by the formula $(C_2H_4O)_b$ when b is an integer. A polyoxypropylene block may generally be represented by the formula $(C_3H_6O)_a$ where a is an integer. The polyoxypropylene block could be for example $(CH_2CH_2CH_2O)_a$, or could be Several POE-POP block copolymers are known to exhibit reverse-thermal gelation properties, and these polymers are particularly preferred for imparting reverse-thermal viscosity and/or reverse-thermal gelation properties to the reverse-thermal viscosity POA formulation. Examples of POE-POP block copolymers include Pluronic™ F68 (a poloxamer 188), Pluronic™ F127 (a poloxamer 407), Pluronic™ L121 (a poloxamer 401), Pluronic™ L101 (a poloxamer 331), and Tetronic™ T1501 (a poloxamine). Tetronic™ T1501 is one example of a POE-POP block copolymer having at least one polymer segment in addition to the polyoxyethylene and polyoxypropylene segments. Tetronic™ T1501 is reported by BASF Corporation to be a block copolymer including polymer segments, or blocks, of polyethylene oxide, poly propylene oxide and ethylene diamine, and is within a class of polymers known as poloxamines.

Some preferred POE-POP block copolymers are generally of the formula:

which block copolymers of this Formula I are generally within the class of polymers known as poloxamers. Molecular weights of poloxamers are often from about 1000 to 16,000 or more, depending upon the particular polymer. In one preferred embodiment, the POE-POP block copolymer is of Formula I and has the property in the presence of water in the proper proportions of being in a liquid form at ambient, or at refrigerated temperatures, and existing in a semi-solid gel form at mammalian body temperatures, and more preferably wherein a and b are integers in the range of 15 to 80 and 50 to 150, respectively. A particularly preferred POE-POP block copolymer, which is a reverse-thermal gelation polymer, for use with the present invention has the following formula:

wherein a and b are integers such that the polyoxypropylene hydrophobe base represented by $(CH_2(CH_3)CHO)_a$ has a molecular weight of about 4,000, as determined by hydroxyl number; the polyoxyethylene chain constituting about 70 percent of the total number of monomeric units in the molecule and where the copolymer has an average molecular weight of about 12,600. Pluronic™ F-127, also known as poloxamer 407, is such a material. In addition, a structurally similar Pluronic™ F-68 may also be used when a reverse-thermal gelation polymer is desired.

In a preferred embodiment, at least the polyoxyalkylene block copolymer is dissolved in the carrier liquid in the delivery composition when the delivery composition is in a flowable medium form for administration. With this preferred embodiment, the polyoxyalkylene block copolymer is selected to be sufficiently soluble in the liquid vehicle to be completely solubilized at the administration temperature. For water as the liquid vehicle, POE-POP block copolymers are preferred containing a relatively large proportion of the hydrophilic POE and a relatively small proportion of the hydrophobic POP, such as would be the case as reflected in the subscript values for the polymers of formulas I and II above. In a preferred embodiment using POE-POP block copolymers, the POE blocks comprise at least 50 weight percent, and more preferably at least 60 weight percent of the POE-POP block copolymer. With many of the polyoxyalkylene block copolymers useful with the present invention, however, at least some of the polymer will adhere to mucosal surfaces within the oral cavity as the delivery composition is warmed after introduction into the patient. This is often, but not always, the case, for example, when the delivery composition exhibits a reverse-thermal gel transition temperature at physiological temperature or lower. In some instances, the delivery composition is diluted by saliva in the oral cavity, or other by other biological fluids at other mucosal sites, at such a fast rate and to such an extent so as to entirely prevent gelling, or prevent even a viscosity increase, from occurring. However, even when gelling or a viscosity increase does not occur, some of the polyoxyalkylene block copolymer and xerostomia therapeutic polymer will adhere to mucosal surfaces. In most situations, the polyoxyalkylene block copolymer will be substantially entirely dissolved in the carrier liquid when the temperature of the composition is at a temperature of about 5° C. There are, however, some situations where it may be desirable to have the delivery composition be in a gel form even at such low temperatures.

The concentration of the polyoxyalkylene block copolymer in the composition will vary depending upon the specific polyoxyalkylene block copolymer and the specific situation. In most situations, however, the delivery composition will include a concentration of the polyoxyalkylene block copolymer that is in a range having a lower limit selected from the group consisting of 1% by weight, 5% by weight, 7% by weight and 10% by weight and having an upper limit selected from the group consisting of 30% by weight, 25% by weight, 20% by weight and 18% by weight. For example, particularly preferred for use of poloxamer 407 (e.g., Pluronic® F-127) and similar polyoxyalkylene block copolymers with a high proportion of polyoxyethylene is in a range of from about 7% by weight to about 20% by weight of the delivery composition.

The xerostomia therapeutic in the delivery composition may be present in any convenient concentration, consistent with the nature and potency of the particular therapeutic and the particular administration/delivery route. For POA formulations, including reverse-thermal viscosity POA formulations, the concentration of the xerostomia therapeutic in the delivery composition is often in a range having a lower limit selected from the group consisting of 0.001% by weight, 0.01% by weight, 0.1% by weight, 1% by weight, 5% by weight and 7% by weight and an upper limit selected from the group consisting of 10% by weight, 15% by weight, 20% by weight and 25% by weight. For NAC in a POA formulation (including in reverse-thermal viscosity POA formulations), a preferred concentration for the NAC in the delivery composition is in a range having a lower limit selected from the group consisting of 1% by weight, 5% by weight and 7% by weight and an upper limit selected from the group consisting of 10% by weight, 15% by weight and 20% by weight.

In POA formulations (including reverse-thermal viscosity POA formulations), the liquid vehicle (typically water) is typically present in the delivery composition at a concentration in a range having a lower limit selected from the group consisting of 50% by weight, 60% by weight and 70% by weight and an upper limit selected from the group consisting of 95% by weight, 90% by weight, 85% by weight and 80% by weight. With respect specifically to reverse-thermal viscosity POA formulations, the relative proportions of the reverse-thermal gelation polyoxyalkylene block copolymer and the liquid vehicle must be selected so that when they are combined into the delivery composition, the delivery composition exhibits the desired reverse-thermal viscosity behavior.

The delivery composition may include, in addition to the xerostomia therapeutic, the polyoxyalkylene block copolymer and the liquid vehicle, one or more other additives, which may for example be one or more of the other components listed previously. The concentration of such additives in the delivery composition, when included, may be any amount not incompatible with the proper functioning of the xerostomia therapeutic, the polyoxyalkylene block copolymer and the liquid vehicle. In most cases, however, each such additive will typically be used at a concentration of not larger than 10 weight percent, often not larger than 5 weight percent or even not larger than 1 weight percent.

For POA formulations, the polyoxyalkylene block copolymer is preferably dissolved in the carrier liquid at the time of application of the delivery composition to the patient, in which case the polyoxyalkylene block copolymer is selected with sufficient solubility in the carrier liquid for the delivery composition at the temperature of administration. In a more preferred embodiment, both the polyoxyalkylene block copolymer and the xerostomia therapeutic are dissolved in the carrier liquid when the delivery composition is administered to the patient. Having the biocompatible polymer and the xerostomia therapeutic codissolved in the carrier liquid ensures intimate mixing of the two materials, which promotes adhesion of the xerostomia therapeutic to surfaces of the oral cavity along with the biocompatible polymer, thereby effectively using the xerostomia therapeutic.

When administered to a patient in the form of a flowable fluid medium, the delivery composition has a relatively low viscosity when the delivery composition is at a temperature for administration to the patient for treatment, and typically such a delivery composition when introduced into the patient has a viscosity of no larger than 60 cP (centipoises), and more preferably no larger than 50 cP. For reverse-thermal viscosity POA formulations, the delivery composition is typically administered at a reduced temperature, and will preferably have a viscosity at 2° C. of no larger than 60 cP and more preferably no larger than 50 cP. For reverse-thermal viscosity POA formulations, the viscosity of the delivery composition will preferably exhibit an increase in viscosity from a viscosity of no larger than 60 cP (and more preferably no larger than 50 cP) to a viscosity of at least 70 cP, or even 80 cp or more (and more preferably even larger) as the temperature of the delivery composition is increased over at least some range of temperatures between 1° C. and the physiological temperature of the patient (e.g., 37° C. for a human patient). For reverse-thermal viscosity POA formulation having a reverse-thermal gelation property, the viscosity will often increase to a level of 90 cp, or even 100 cP or more with an increase in temperature from below to above the reverse-thermal gel transition temperature.

For oral mucosal delivery using a reverse-thermal viscosity POA formulation having a reverse-thermal gelation property, the delivery composition can be used as a mouth rinse at a temperature below the reverse-thermal gel transition temperature, whereupon the delivery composition will ordinarily become more viscous or even gelatinous as it warms inside the mouth. Not all aspects of the invention when treating for oral xerostomia are so limited, however. For example, in some instances the delivery composition may not become more viscous or gelatinous inside the mouth of the patient, but a reverse-thermal gelation polyoxyalkylene block copolymer will still provide some protection to the oral xerostomia therapeutic and enable contact and permeation of the xerostomia therapeutic within the oral mucosa.

Solutes can be incorporated into the delivery composition of the present invention to stabilize the xerostomia therapeutic. Stabilizing solutes such as those that modify the pH of the delivery composition or a second antioxidant, may aid in protecting and stabilizing the therapeutic by keeping it in a reduced, thus active, form. Furthermore, pH modification, inclusion of an antioxidant (in addition to the xerostomia therapeutic), or inclusion of a solute such as sucrose may not only aid in protecting and stabilizing the therapeutic, but also allow a reverse-thermal gelation polyoxyalkylene block copolymer to form solutions at suitable viscosities at lower concentrations than needed in water or buffer alone and/or to change the transition temperature at which thermal gelation occurs. Thus, the working range of a reverse-thermal gelation polyoxyalkylene block copolymer concentration can be widened and the transition temperature modified.

It is known that in some cases a gel will not form when the concentration of reverse-thermal gelation polyoxyalkylene block copolymer in water or dilute buffer is outside a particular range, e.g., equal to or less than about 15% by weight in water for Pluronic™ F127. However, by introducing therapeutic-stabilizing solutes, or other components, into a POA formulation, the transition temperature may be manipulated, while also lowering the concentration of polyoxyethylene-polyoxypropylene block copolymer that is necessary to form a gel. Also, the presence of the xerostomia therapeutic, a penetration enhancer and other additives, tend to alter the viscosity behavior of the delivery composition, often by lowering the concentration of the reverse-thermal gelation polymer required to impart reverse-thermal gelation properties to a delivery composition.

The following example is given to illustrate the present invention. It should be understood that the invention is not to be limited to the specific conditions or details described in the example.

EXAMPLE

This example describes a clinical trial in which the formulation and use of the antioxidant NAC within a Pluronic® F127 (F127) delivery matrix (formulations identified below as RK-0202) were assessed for preventing and reducing the incidence of oral mucositis in a patient population that received radiation therapy (RT) as a course of treatment for head and neck cancer. The formulation was found to significantly reduce the incidence of severe oral mucositis as well as the incidence of xerostomia. The reduction of xerostomia was unexpected.

Study Design

A double-blind, placebo controlled trial was undertaken in patients with head and neck cancer. The objectives of the trial were to assess the efficacy and tolerability of RK-0202 on radiation induced oral mucositis and other toxicities. Ninety-four (94) patients with head and neck cancer were randomized to treatment with placebo or two different dosage strengths of NAC in RK-0202. Twenty-seven patients received RK-0202 containing 5% by weight NAC, 37 received RK-0202 10% by weight NAC, and 29 received placebo. Patients began dosing prior to their first radiation treatment and continued dosing six times daily throughout radiation. Oral mucositis and other radiation induced toxicities were assessed twice weekly throughout the radiation course.

Patients

The study was conducted at 15 sites in North America (12 in the US and 3 in Canada). The protocol was approved by the institutional review board at each site. All patients gave written informed consent before entry and before study-related procedures were performed. Eligible patients were at least 18 years of age, had a Karnofsky performance-status score of at least 60 and were scheduled to receive a total, external beam radiation dose of at least 60 Gy for head and neck carcinoma. The planned radiation volume had to include at least 3 oral qualifying sites, a qualifying site was defined as one that would receive at least 60 Gy to 2 $cm^2$. Radiotherapy could consist of 1.8-2.2 Gy per day in single fractions and up to 3.3 Gy/day during concurrent boost. Patients were excluded from the study if they were to receive concomitant chemotherapy, amifostine or salagen, or if they had evidence of oral mucositis at baseline, prior radiotherapy to the head and neck. Patients with a medical, sociological, or psychological impediment to probable compliance with protocol were also excluded. Concomitant use of oral antifungals, topical and systemic analgesics as well as palliative mouth rinses consisting of viscous lidocaine, milk of magnesia, baking soda and salt were allowed.

A standard oral care protocol was followed at each institution. Patients were instructed to brush their teeth twice daily, floss once daily, apply fluoride treatments and refrain from wearing dentures. Commercial mouthwashes were prohibited.

Study Drug Formulation and Manufacture

Table 1 shows the compounds and percentages of each compound used for the formulations of 5% and 10% RK-0202 and placebo.

TABLE 1

| Ingredient | Placebo | 5% NAC | 10% NAC |
|---|---|---|---|
| NAC | None | 5.0 | 10.0 |
| F127 | 13.0 | 13.0 | 13.0 |
| $CaNa_2EDTA$ | 0.09 | 0.09 | 0.09 |
| Methyl Paraben | 0.20 | 0.20 | 0.20 |
| Na Citrate | 0.29 | 0.29 | 0.29 |
| NaCl | 1.418 | None | None |
| NaOH | None | 1.225 | 2.45 |
| Sucralose | 0.050 | 0.050 | 0.050 |
| Lemon Extract | 2.40 | 2.40 | 2.40 |
| Water (q.s.) | 82.552 | 77.745 | 71.520 |

All values as % w/w

Figure 1:
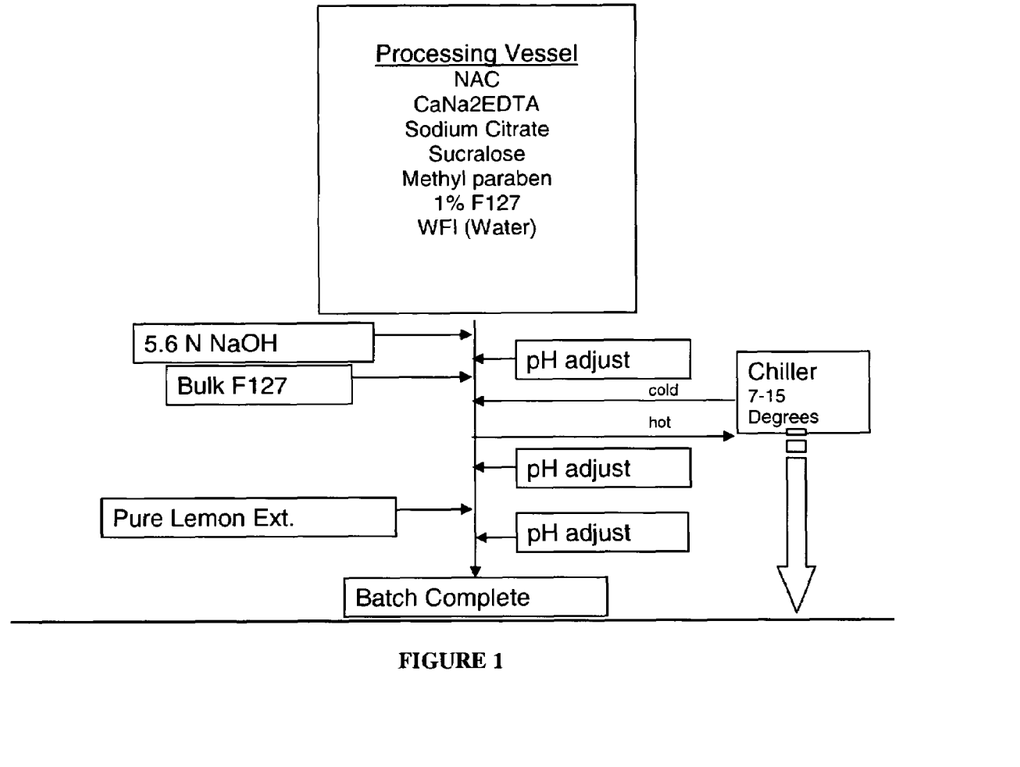
FIG. 1 is a process diagram for preparation of batches of delivery compositions for a clinical study that is the subject of the Example.

FIG. 1 is a diagram summarizing the processing used for production of the RK-0202 formulations for the Phase 2 clinical trial. With reference to FIG. 1, all raw materials are weighed and placed into dispensing containers, from which the raw materials are withdrawn for preparation of the RK-0202 formulations. RK-0202 formulations are prepared in batches in a processing vessel. As shown in FIG. 1, in the processing vessel an initial solution of 1% F-127 in water is prepared also containing the calcium disodium EDTA, sodium citrate, methyl paraben (preservative) and Sucralose (sweetener). Then the NAC is added to the processing tank. NaOH is added with a chiller adjusted to avoid temperature excursions above 15° C. caused by heat of dissolution. A first pH adjustment is made to maintain a pH range of 5.5-6.0. The remainder of the F127 for the batch is added and the processing vessel is chilled as the pH is monitored and adjusted as needed to maintain pH of 5.5-6.0. The lemon extract (flavoring) is added and a final pH adjustment is made to complete the batch.

The batch is filtered and filled into containers, which are sealed, labeled and stored at 2-8° C. in cardboard boxes for clinical use.

Dosing of Study Drug

Patients began taking study drug at the start of their radiotherapy (RT), prior to the first radiation fraction. Patients were instructed to rinse with study drug (10 ml) for 1 minute, approximately six times each day or once every 2-3 hours while awake. Study drug was not to be swallowed. Patients dosed with study drug every day throughout their radiotherapy treatment.

Oral mucositis was assessed with the World Health Organization (WHO) oral toxicity scale (Miller AB et al, 1981), the National Cancer Institute's (NCI) Common Toxicity Criteria for radiation induced oral mucositis and the Oral Mucositis Assessment (OMAS).

Adverse events were assessed twice weekly and graded according to the NCI Common Toxicity Criteria for Adverse Events (CTCAE Version 3). Xerostomia was recorded as an adverse event in this trial and was defined according to the NCI CTCAE criteria.

Efficacy and Safety End Points

Analyses of all efficacy and safety end points included all qualifying patients who underwent randomization and received at least one dose of study medication. The incidence of severe mucositis was analyzed using a time-to-failure analysis, with cumulative RT dose substituted for time, and the interval specified as 0-60 Gy. Patients with WHO or NCI grade 0, 1, or 2 oral mucositis were defined as successes and those with grade ≧3 as failures. The primary comparisons were between the placebo and RK-0202 with 10% NAC groups.

Results

Figure 2:
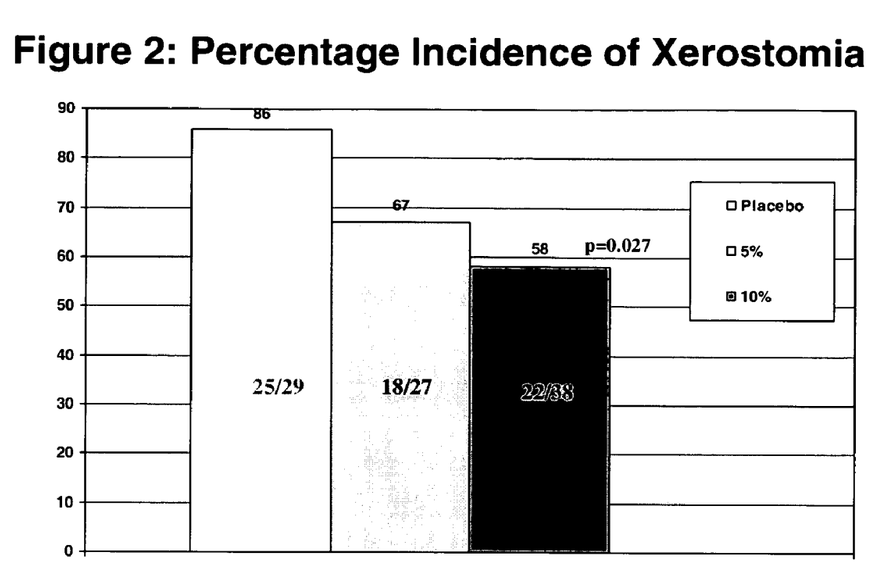
FIG. 2 is a graph of incidence of xerostomia in subjects taking placebo or compositions containing 5 weight percent or 10 weight percent N-acetylcysteine during the clinical study that is the subject of the Example.

RK-0202 significantly reduced the incidence of radiation-induced xerostomia compared with placebo. Eighty-six percent of patients receiving placebo reported xerostomia during the study compared with 63% of all patients receiving RK-0202, including 67% of patients receiving RK-0202 with 5% NAC and 58% of patients receiving RK-0202 with 10% NAC (p=0.027 for 10% RK-0202 vs. placebo). P values were determined by Fisher's exact test. These results for xerostomia are summarized graphically in FIG. 2. The incidence of World Health Organization (WHO) grade 3 or 4 oral mucositis by a cumulative radiation dose of 50 Gy was 56% on placebo compared with 25% on RK-0202 containing 10% NAC (p=0.041). Compared with placebo, RK-0202 also significantly reduced the incidence of severe mucositis according to the NCI toxicity scale, 88% on placebo compared to 42% on RK-0202 (p=0.005). Furthermore, RK-0202 significantly reduced the need for external feeding tubes to maintain nutritional status, 23% on placebo required feeding tubes as compared to 3% of patients on RK-0202. Table 2 summarizes adverse events during the clinical study. Also significant and surprising is the reduced incidence of weight loss, anorexia and anxiety among patients receiving RK-0202, as shown in Table 2.

TABLE 2

Most Frequently Occurring Adverse Events by NCI Body System and Preferred Term

| Analysis N All Adverse Events >20% Incidence N (%) | Placebo 29 | 5% NAC 27 | 10% NAC 38 | 10% NAC vs. placebo (Fisher's exact p) |
|---|---|---|---|---|
| Constitutional Symptoms | | | | |
| Fatigue | 15 (52) | 11 (41) | 18 (47) | |
| Weight Loss | 14 (48) | 11 (41) | 4 (11) | p = 0.0009 |
| Dermatology/Skin | | | | |
| Dermatitis | 13 (45) | 13 (48) | 20 (53) | |
| Alopecia | 1 (3) | 3 (11) | 5 (13) | |
| Gastrointestinal | | | | |
| Xerostomia | 25 (86) | 18 (67) | 22 (58) | p = 0.027 |
| Dysgeusia | 14 (48) | 13 (48) | 17 (45) | |
| Nausea | 15 (52) | 14 (52) | 11 (29) | p = 0.082 |
| Dysphagia | 10 (34) | 11 (41) | 15 (39) | |
| Constipation | 13 (45) | 8 (30) | 10 (26) | |
| Odynophagia | 11 (38) | 10 (37) | 10 (26) | |
| Anorexia | 14 (48) | 9 (33) | 7 (18) | p = 0.016 |
| Vomiting | 7 (25) | 11 (41) | 6 (16) | |
| Dehydration | 6 (21) | 7 (26) | 3 (8) | |
| Oral Cavity | 5 (17) | 2 (7) | 2 (5) | |
| Mucositis Infection | | | | |
| Candidiasis | 9 (31) | 5 (19) | 9 (24) | |
| Lymphatics | | | | |
| Edema, Head & Neck | 4 (14) | 4 (15) | 11 (29) | |
| Neurology | | | | |
| Headaches | 9 (31) | 8 (30) | 8 (21) | |
| Anxiety | 9 (31) | 5 (19) | 1 (3) | p = 0.0035 |
| Pain | | | | |
| Throat | 10 (34) | 8 (30) | 12 (32) | |
| Pulmonary/Upper Respiratory | | | | |
| Cough | 3 (10) | 3 (11) | 5 (13) | |
| Study Drug | | | | |
| Mouth Burning | 5 (17) | 4 (15) | 10 (26) | |

Note: Column header counts and denominators are the number of subjects in the intent to treat population. A subject is counted at most once within each NCI body system and preferred term

CONCLUSIONS

RK-0202 significantly reduced the incidence of radiation induced xerostomia and severe oral mucositis in patients treated with radiotherapy for head and neck cancer. The effect of RK-0202 on xerostomia is potentially due to protection of superficial salivary function, stimulation of salivary flow and decreased viscosity of saliva.

The description of the invention, including the foregoing example, has been presented for purposes of illustration and description. Moreover, the description is not intended to limit the variations and modifications commensurate with the above teachings, and the skill or knowledge in the relevant art are within the scope of the present invention. It will be apparent to those skilled in the art that various modifications and variations can be made in the methods and compositions of the present invention without departing from the spirit or scope of the present invention, and thus it is intended that the present invention cover modifications and variations of this invention provided they come within the scope of the appended claims and their equivalents. Also, the preferred embodiment(s) described hereinabove are intended to explain the best mode known of practicing the invention and to enable others skilled in the art to utilize the invention in various embodiments and with the various modifications required by their particular applications or uses of the invention. Moreover, to the extent that features are not functionally incompatible, it is contemplated within the scope of the present invention that any feature of any disclosed embodiment is combinable in any combination with any feature of any other embodiment. It is intended that the appended claims be construed to include alternate embodiments to the extent permitted by the prior art. Use of the terms "comprise," "include," "contain," "have" and variations of those terms are intended to be open-ended, and used to indicate the presence of an attribute, feature or component, but not to the exclusion of the presence of other possible attributes, features or components.

What is claimed is:

1. A method for treating a patient for xerostomia, the method comprising:
administering to the patient a therapeutically effective amount of an active agent for treating xerostomia, wherein the active agent is a sulfur-containing antioxidant effective for treating for xerostomia.

2. The method of claim 1, wherein the sulfur-containing antioxidant is N-acetylcysteine.

3. The method of claim 1, wherein during the administering, the sulfur-containing antioxidant is in a delivery composition that is administered to the patient, the delivery composition comprising a liquid vehicle and a polyoxyalkylene block copolymer.

4. The method of claim 3, wherein the delivery composition is in the form of a flowable fluid medium when the delivery composition is administered to the patient during the administering.

5. The method of claim 3, wherein the sulfur-containing antioxidant is dissolved in the liquid vehicle when the delivery composition is administered to the patient during the administering.

6. The method of claim 3, wherein the polyoxyalkylene block copolymer is dissolved in the liquid vehicle when the delivery composition is administered to the patient during the administering.

7. The method of claim 3, wherein the liquid vehicle is water.

8. The method of claim 3, wherein the polyoxyalkylene block copolymer is a polyoxyethylene-polyoxypropylene block copolymer.

9. The method of claim 8, wherein polyoxyethylene comprises at least 50 weight percent of the polyoxyethylene-polyoxypropylene block copolymer.

10. The method of claim 8, wherein the polyoxyalkylene block copolymer is a reverse-thermal gelation polymer, and the delivery composition exhibits reverse-thermal viscosity behavior over some temperatures in a range of from 1° C. to 37° C.

11. The method of claim 10, wherein the delivery composition has a reverse-thermal gelation property and a reverse-thermal gel transition temperature in a range of from 1° C. to 37° C.

12. The method of claim 8, wherein the polyoxyalkylene block copolymer is a poloxamer 407.

13. The method of claim 3, wherein the sulfur-containing antioxidant comprises from 0.001 weight percent to 25 weight percent of the delivery composition.

14. The method of claim 3, wherein the sulfur-containing antioxidant comprises from 5 weight percent to 15 weight percent of the delivery composition.

15. The method of claim 3, wherein the polyoxyalkylene block copolymer comprises from 1 weight percent to 30 weight percent of the delivery composition.

16. The method of claim 3, wherein the polyoxyalkylene block copolymer comprises from 7 weight percent to 18 weight percent of the delivery composition.

17. The method of claim 3, wherein the liquid vehicle comprises from 50 weight percent to 90 weight percent of the delivery composition.

18. The method of claim 16, wherein the liquid vehicle comprises from 60 weight percent to 85 weight percent of the delivery composition.

19. The method of claim 3, wherein the delivery composition is in the form of an oral rinse solution when administered the delivery composition is administered to the patient during the administering, and the administering comprises introducing the oral rinse solution into the oral cavity of the patient.

20. The method of claim 1, wherein the sulfur-containing antioxidant is at a temperature in a range of 1° C. to 10° C. when administered to the patient during the administering.

21. The method of claim 1, wherein the administering comprises introducing the sulfur-containing antioxidant into the oral cavity of the patient for oral mucosal delivery of the sulfur-containing antioxidant.

22. The method of claim 1, wherein the administering comprises subcutaneous placement of the sulfur-containing antioxidant in the vicinity of at least one salivary gland of the patient.

23. The method of claim 1, wherein the administering comprises injection of the sulfur-containing antioxidant directly into at least one salivary gland of the patient.

* * * * *